(12) United States Patent
Knodel (10) Patent No.: US 7,462,185 B1
(45) Date of Patent: Dec. 9, 2008

(54) INTRAVASCULAR STAPLING TOOL

(75) Inventor: Bryan D. Knodel, Flagstaff, AZ (US)

(73) Assignee: Cardican Inc., Redwood City, CA (US)

( * ) Notice: Subject to any disclaimer, the term of this patent is extended or adjusted under 35 U.S.C. 154(b) by 376 days.

(21) Appl. No.: 11/022,551

(22) Filed: Dec. 23, 2004

(51) Int. Cl.
*A61B 17/10* (2006.01)

(52) U.S. Cl. ..................... 606/139; 227/175.1

(58) Field of Classification Search ............ 606/108, 606/139, 142, 151, 143; 623/1.23; 128/898; 227/175.1–175.4, 176.1–182, 19
See application file for complete search history.

(56) References Cited

U.S. PATENT DOCUMENTS

| | | | | |
|---|---|---|---|---|
| 4,396,139 A | * | 8/1983 | Hall et al. ..................... 227/19 |
| 5,158,567 A | * | 10/1992 | Green ........................ 606/219 |
| 5,792,094 A | * | 8/1998 | Stevens et al. ............. 604/4.01 |
| 5,861,005 A | * | 1/1999 | Kontos ....................... 606/219 |
| 5,972,023 A | * | 10/1999 | Tanner et al. ............... 606/219 |
| 6,149,660 A | * | 11/2000 | Laufer et al. ................ 606/143 |
| 6,352,541 B1 | * | 3/2002 | Kienzle et al. .............. 606/143 |
| 6,482,224 B1 | | 11/2002 | Michler et al. |
| 2005/0090834 A1 | | 4/2005 | Chiang et al. |
| 2005/0090843 A1 | | 4/2005 | Bolduc |
| 2005/0187613 A1 | | 8/2005 | Bolduc et al. |

* cited by examiner

*Primary Examiner*—(Jackie) Tan-Uyen T. Ho
*Assistant Examiner*—Melanie Tyson
(74) *Attorney, Agent, or Firm*—Brian A. Schar (57) ABSTRACT

An intravascular stapler may include a catheter connected to a stapler head and to a handle. The stapler head may be introduced into the vasculature of a patient through an opening in the femoral artery or other part of the vasculature, and advanced to a treatment site such as an abdominal aortic aneurysm via the catheter.

8 Claims, 8 Drawing Sheets

INTRAVASCULAR STAPLING TOOL

FIELD OF THE INVENTION

The present invention relates generally to medical devices, and more particularly to an intravascular stapler.

BACKGROUND

Abdominal aortic aneurysm (AAA) is an abnormal ballooning of the abdominal portion of the aorta, which is the major artery routing blood from the heart to all organs. Abdominal aortic aneurysm involves a dilation, stretching, or ballooning of the abdominal aorta, which is the section of the aorta residing in the abdominal cavity. Causes of abdominal aortic aneurysm include infection, tissue disease (such as atherosclerosis) resulting in weakening of the connective tissue component of the arterial wall, trauma, and Marfan's syndrome. Abdominal aortic aneurysm can affect anyone, but it is most often seen in men aged 40 to 70. Most commonly, abdominal aortic aneurysms occur in the portion of the vessel below the renal artery origins, and may extend into the vessels supplying the hips and pelvis.

A common complication of AAA is rupture. This is a medical emergency where the aneurysm breaks open, resulting in profuse bleeding. Aortic rupture is life-threatening; the likelihood of death after rupture is generally considered to be 80-90%. Once an aneurysm reaches 5 cm in diameter, it is usually considered necessary to treat it to prevent rupture.

Surgical repair or replacement of the section of aorta that includes the aneurysm is recommended for patients with symptoms and for patients with aneurysms greater than 5 cm in diameter, as they are at high risk of fatal rupture. Because surgery for abdominal aortic aneurysm is risky, the surgeon may wait for the aneurysm to expand to a size at which the risk of complications exceeds the risk of surgery. Below 5 cm, the risk of the aneurysm rupturing is lower than the risk of conventional surgery in patients with normal surgical risks. However, it is undesirable to wait for a known AAA to get worse in order to treat it.

Placement of an AAA graft is also a treatment option. An AAA graft is a tube or tubelike structure placed inside the aorta. Its placement can be performed without an abdominal incision, with specialized catheters that are introduced through arteries at the groin. However, not all patients with abdominal aortic aneurysms are candidates for grafts, however. Further, some AAA grafts in the past have had difficulties that have resulted in their removal from the marketplace, such as breakage of the hooks that hold the AAA graft in place in the aorta, and difficulties with the tools for deploying the AAA grafts.

BRIEF DESCRIPTION OF THE DRAWINGS

The use of the same reference symbols in different figures indicates similar or identical items.

DETAILED DESCRIPTION

Intravascular Stapling Tool

Figure 1:
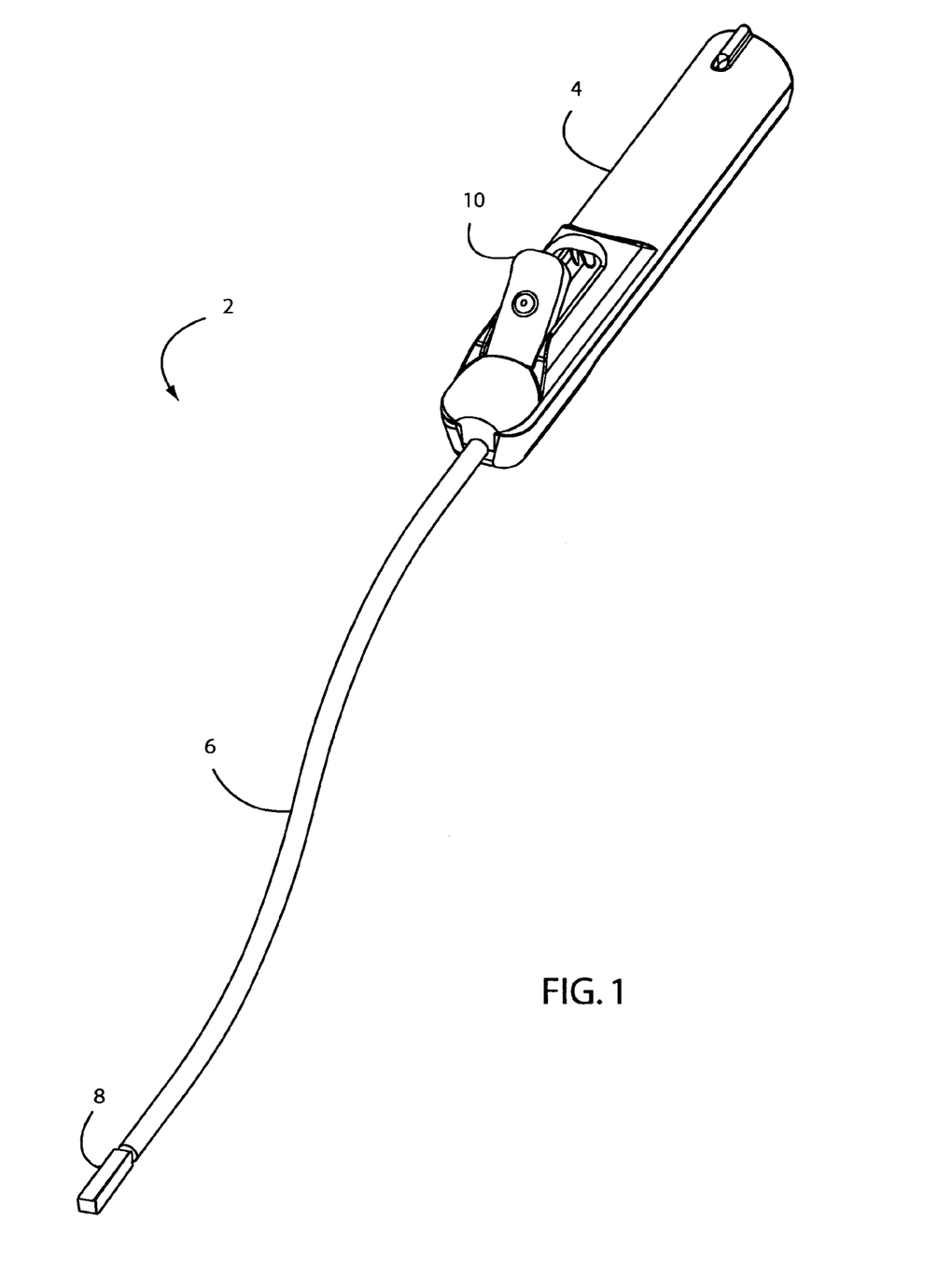
FIG. 1 is a perspective view of an intravascular stapling tool having a stapler head connected to a handle by a catheter.

Referring to FIG. 1, an exemplary intravascular stapling tool 2 is shown. The intravascular stapling tool 2 includes a handle 4, a catheter 6 connected to the handle 4, and a stapler head 8 connected to both the handle 4 and the catheter 6. The intravascular stapling tool 2 may be configured differently, if desired. The handle 4 and the stapler head 8 are both fixed to the catheter 6. Alternately, the handle 4 and/or the stapler head 8 may be detachable from the catheter 6 to allow for interchangeability of these components. At least part of the handle 4 and/or the stapler head 8 may be constructed from materials that can be sterilized, such as by an autoclave, and reused. The handle 4 may assume any appropriate configuration; the shape and configuration of the handle 4 described herein is exemplary and not limiting. The handle 4 may include a trigger 10 that provides for actuation of the intravascular stapling tool 2 based solely on a single input from the user to that trigger 10, as described in greater detail below. Alternately, one or more other or additional inputs may be utilized to actuate the intravascular stapling tool 2. For example, actuation of the intravascular stapling tool 2 may be based on an input to one or more buttons in addition to the trigger 10.

Figure 2:
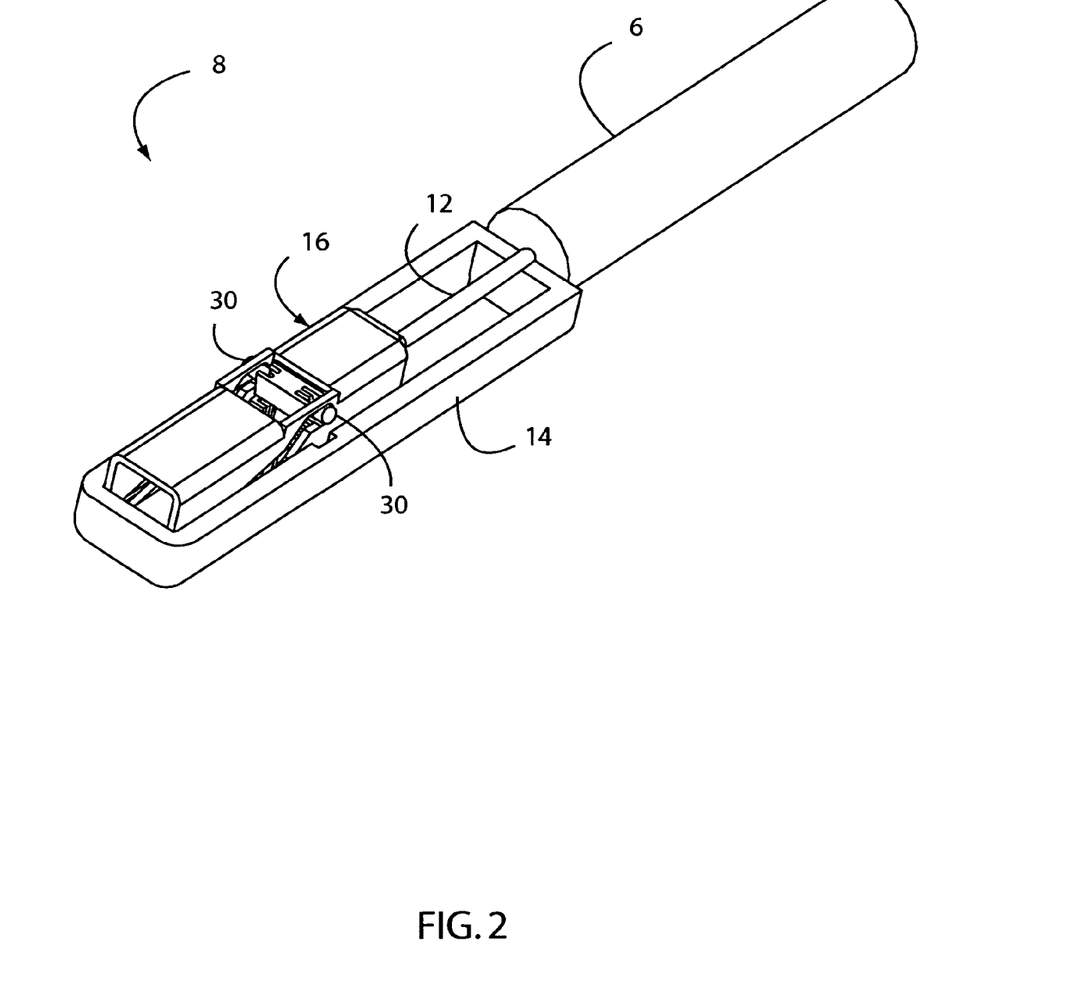
FIG. 2 is a perspective cutaway view of the stapler head of FIG. 1.

The catheter 6 is a standard catheter such as used in coronary or peripheral vascular procedures. As such, the catheter 6 is stiff enough to push the stapler head 8 to the desired position in the vasculature through an opening in the femoral artery or other arty, and flexible enough to move through the vasculature without damaging the tissue thereof. The catheter 6 is non-rigid. The catheter 6 is a tubular structure having one or more lumens therethrough. Alternately, the catheter 6 may be configured in any other suitable manner. Referring also to FIG. 2, one or more force transmission members 12 extend through at least one lumen of the catheter 6. Advantageously, a single force transmission member 12 is utilized. Where multiple force transmission member 12 are utilized, each force transmission member 12 may extend through a separate lumen of the catheter 6, or multiple force transmission members 12 may extend through one lumen of the catheter 6. At least one force transmission member 12 may be a cable 12, such as a braided stainless steel wire cable. The catheter 6 may be configured to accommodate a standard guidewire that may be used to guide the catheter 6 and stapler head 8 to a treatment site. As one example, the catheter 6 may include a lumen therein that is configured to receive and travel along the guidewire. As another example, a tube or tubes may be attached to the outer surface of the catheter 6, where such a tube or tubes receive the guidewire.

Referring also to FIG. 2, the stapler head 8 may be attached to the distal end of the catheter 6. The stapler head 8 may be attached to the stapler head 8 in any suitable manner. Alternately, the stapler head 8 may be attached to the catheter 6 at a location other than the distal end of the catheter 6. The stapler head 8 includes a housing 14. A portion of the housing 14 is cut away to better illustrate the interior of the stapler head 8. The housing 14 may have any suitable shape. As one example, the housing 14 is shaped as the shell of a substantially rectangular solid, with smoothed or curved vertices to protect tissue. At least one force transmission member 12 may extend out of the distal end of the catheter 6 into the interior of the housing 14.

Figure 3:
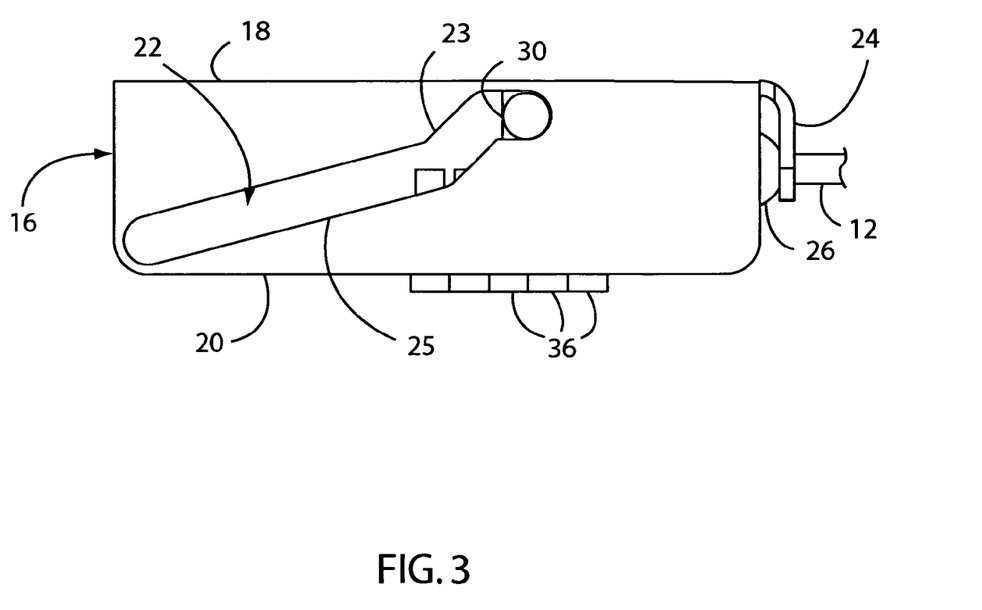
FIG. 3 is a side view of a slider of the stapler head in a first position.

Referring also to FIG. 3, a slider 16 is movable within the housing 14, and may be connected to at least one force transmission member 12. The slider 16 may be substantially U-shaped as viewed longitudinally, with an upper surface 18 and two walls 20 extending downward from the upper surface 18, one from either edge of the upper surface 18. The terms "upper," "lower," "downward," "upward," "vertical," "horizontal" and the like are used for convenience only, in reference to the position of various components in the Figures. The use of these terms does not limit the orientation of the stapler head 8 in use. Alternately, the slider 16 may be shaped differently. At least one wall 20 of the slider 16 includes at least one slot 22 defined therein. A proximal wall 24 may extend downward from the upper surface 18 at or near the proximal end of the slider 16. The proximal wall 24 may be connected to at least one force transmission member 12 in any suitable manner. As one example, the force transmission member 12 may be a cable 12 that extends through an opening (not shown) in the proximal wall 24 and is crimped to the proximal wall 24. As another example, an end of the cable 12 is connected to an termination element 26. The termination element 26 is wider than the opening in the proximal wall 24 through which the cable 12 extends. Thus, the termination element 26 prevents the cable 12 from slipping out of the opening in the proximal wall 24. As another example, the end of the cable 23 may be knotted, forming a knot having a diameter larger than that of the opening in the proximal wall 24. As another example, the cable 12 is connected to the proximal wall by welding or by adhesive. The cable 12 is routed into the stapler head 8 in such a way that tension exerted on the cable 12 causes the slider 16 to move proximally. Alternately, at least one force transmission member 12 is connected to a different location on the slider 16, directly or indirectly.

Figure 4:
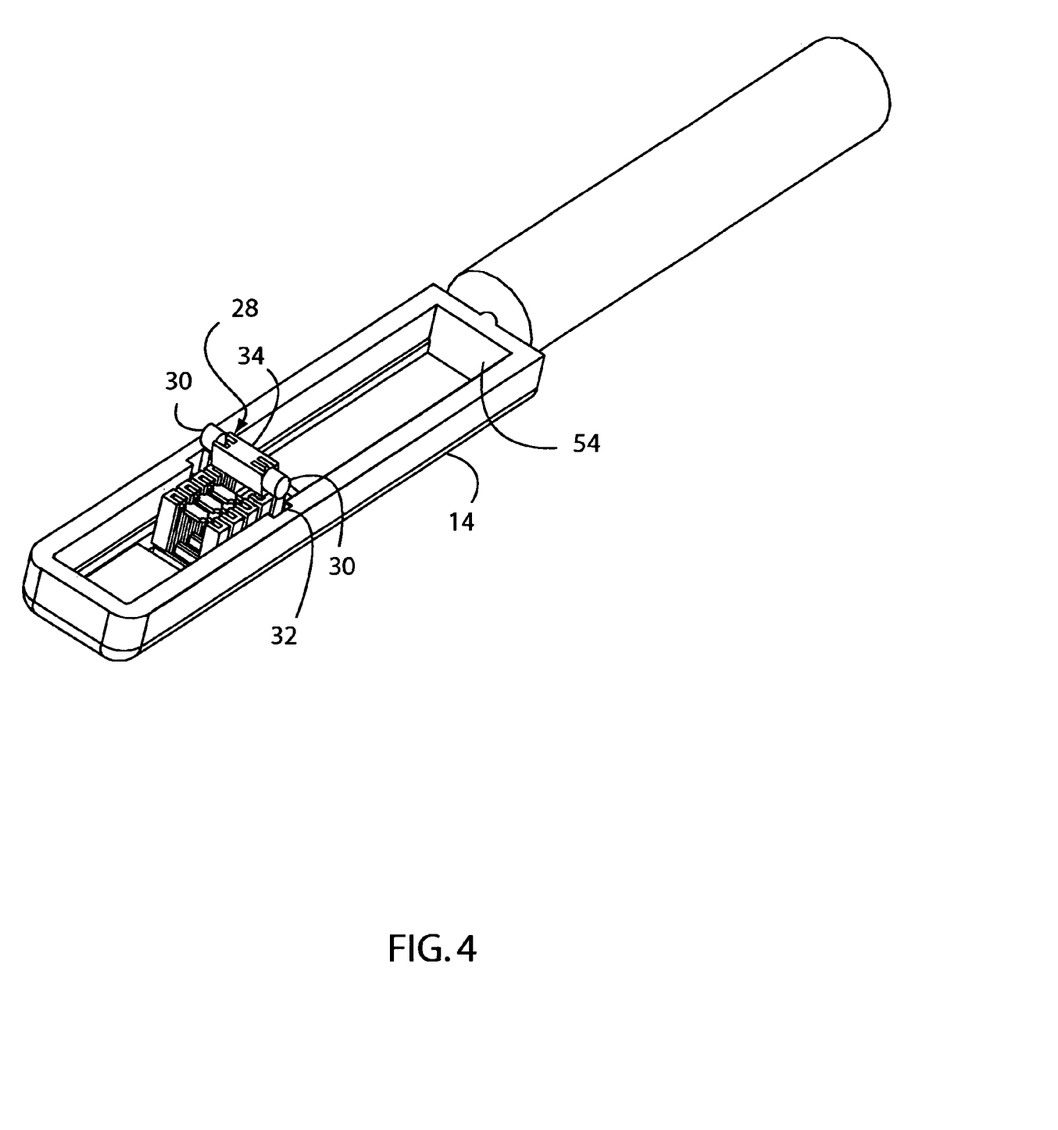
FIG. 4 is a perspective cutaway view of the stapler head of FIG. 1, with the slider omitted for clarity.

Referring also to FIG. 4, a driver 28 is movable within the housing 14. The driver 28 includes at least one post 30 extending laterally from a central body 34. Each post may be substantially cylindrical, or may be shaped differently. At least one groove 32 is defined in the inner surface of the housing 14, oriented substantially in the vertical direction. Each groove 32 is sized and shaped to receive a corresponding post 30 of the driver 28. Advantageously, posts 30 extend laterally from the driver 28 in both directions, and each is received in the corresponding groove 32 in the housing. The groove 32 constrains motion of the corresponding post 30 along the direction of the groove 32. Thus, the use of two substantially vertical grooves 32 with a driver 28 having two lateral posts 30 extending therefrom constrains the motion of the driver 28, allowing the driver 28 to move up and down along the grooves 32 but substantially restricting the motion of the driver 28 in the longitudinal or lateral directions. That is, the driver 28 is constrained to move substantially perpendicular to the longitudinal axis of the stapler head 8. Alternately, the grooves 32 are oriented differently, and thereby constrain the motion of the driver 28 differently.

Referring also to FIG. 3, the driver 28 may be positioned within the slider 16. That is, the driver 28 may be positioned below the upper surface 18 of the slider 16, and between the walls 20 of the slider 16. Each post 30 of the driver 28 extends through a corresponding slot 22 in the wall 20 of the slider 16, then into the corresponding groove 32 in the housing 14. In this way, at least one wall 20 is positioned between the central body 34 of the driver 26 and a groove 32 in the inner surface of the housing 14.

Figure 5:
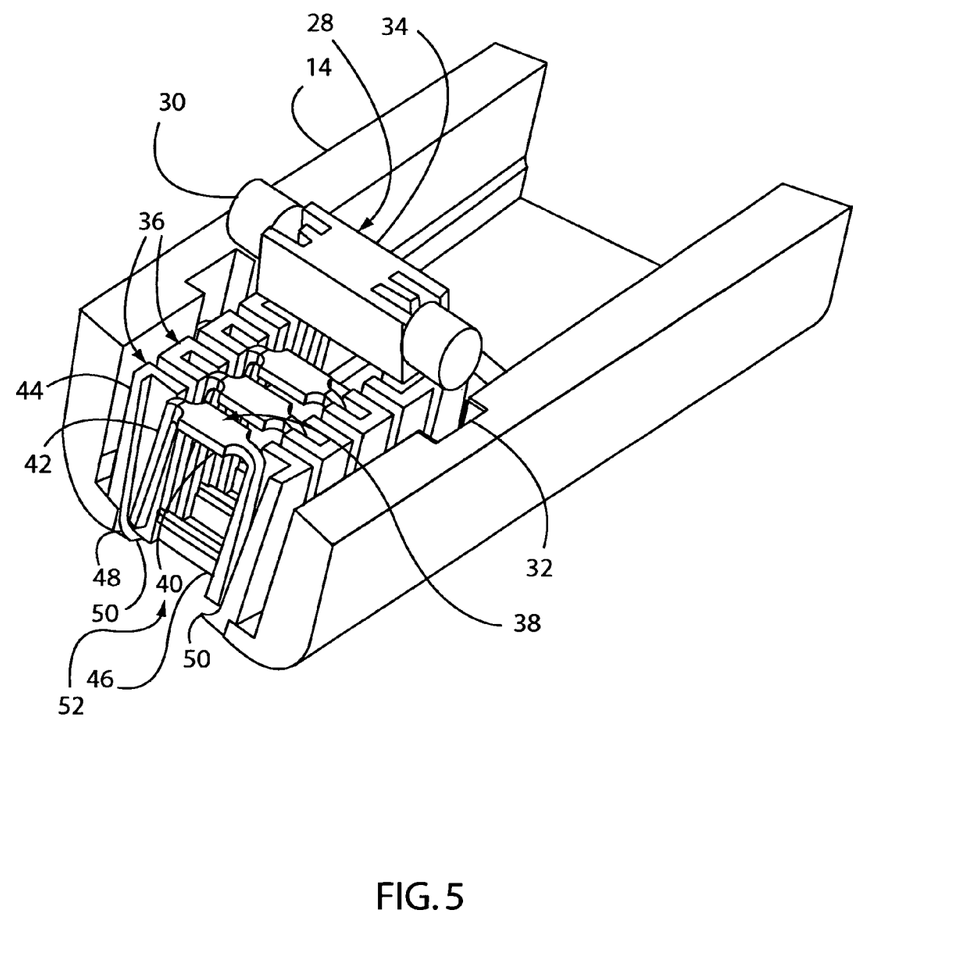
FIG. 5 is a detail perspective cutaway view of the stapler head of FIG. 1, with the slider and the distal end of the stapler head omitted for clarity.

Referring to FIGS. 4-5, at least one holder 36 is positioned within the housing 14. Each holder 36 holds a staple 38. The staples 38 may be shaped in any suitable manner, and at least one staple 38 may be shaped differently than one or more other staples 38. As one example, at least one staple 38 has a substantially planar base 40, with a tine 42 extending laterally from each side of the base 40. Each tine 40 is narrower than the width of the base 40, as measured in the longitudinal direction. Alternately, at least one staple 38 is configured differently.

Each holder 36 may be shaped in any manner that allows it to hold a staple 38, and at least one holder 36 may be shaped differently than one or more other holders 36. As one example, a holder 36 may include two substantially upwardly-extending columns 44 connected to a substantially laterally-extending base 46. The columns 44 may have a generally U-shaped profile looking downward into them, where a tine 42 of the staple 38 is held by a column 44 between the arms of the U. The open sides of the U-shaped columns 44 face each other, such that each column 44 of a holder 36 holds a tine 42 of the corresponding staple 38. Alternately, the columns 44 are configured differently to hold the corresponding staple 38. The inner surface of each column 44 facing the longitudinal centerline of the housing 14 may be a ramp element 48. The ramp element 48 is smoothly curved inward, moving downward along the column 44. That is, the distance between two opposed ramp elements 48 in a holder 36 is less at the bottom of the holder 36 than at the top of the holder 36. This curvature assists in deployment of the staple 38. At the bottom of the holder 36, each ramp element 48 terminates in a foot 50. Taken together, the feet 50 of each holder 36, in conjunction with a portion of each ramp element 48 in proximity to each foot 50, may be characterized as an internal anvil. Thus, at least one holder 36 includes an internal anvil for forming the staple 38 deployed therefrom.

The base 46 of at least one holder 36 may be two substantially laterally-extending bars on opposite sides of two laterally-spaced columns 44. Advantageously, the holder 36 is fabricated from a single piece of material, but the columns 44 and base 46 initially may be separate pieces that are connected in any suitable manner. The base 46 of each holder 36 contacts the base 46 of at least one adjacent holder 36. In this manner, force between adjacent holders 36 is transmitted between the bases 46 of those holders 36. Alternately, adjacent holders 36 contact one another in one or more different or additional locations. The holders 36 separate adjacent staples 38 from one another such that force is transmitted between holders 36, not between staples 38. That is, where a longitudinal force is applied to one holder 36, that force is transmitted to the adjacent holder 36 without exerting any force on the staple 38 within each holder 36. In this way, the design and fabrication of the staples 38 may be simplified, as the staples 38 do not transmit forces among one another. That is, each holder 36 substantially isolates the staple 38 that it holds from force transmitted from any adjacent holder 36. The staples 38 may be spaced apart from one another without touching, as a result of their being held within the holders 36. Alternately, at least one staple 38 may contact one or more adjacent staples 38.

Where more than one holder 36 is utilized, they are arranged longitudinally, such that one holder 36 is the most proximal holder 36, and that one holder 36 is the most distal holder 36. Alternately, at least one of the holders 36 may be positioned differently relative to at least one of the other holders 36. The holder or holders 36 are positioned within the housing 14 such that the upper boundary of each holder 36 is at a lower height than the lower boundary of the driver 28, when the driver 28 is in a ready position. In the ready position, the driver 28 is above the staple 38, but is not applying a deployment force to the staple 38. Alternately, the holder or holders 36 may be positioned differently within the housing 14. An ejection aperture 52 is defined through the bottom surface of the housing 14. The ejection aperture 52 is directly underneath the driver 28, such as where the groove or grooves 32 are substantially vertical. Alternately, the longitudinal position of the ejection aperture 52 may be offset from the longitudinal position of the driver 28. Because the driver 28 is constrained to move along the groove or grooves 32, the ejection point of each staple 38 from the corresponding holder 36 is always known, and that ejection point is the ejection aperture 52.

Figure 6:
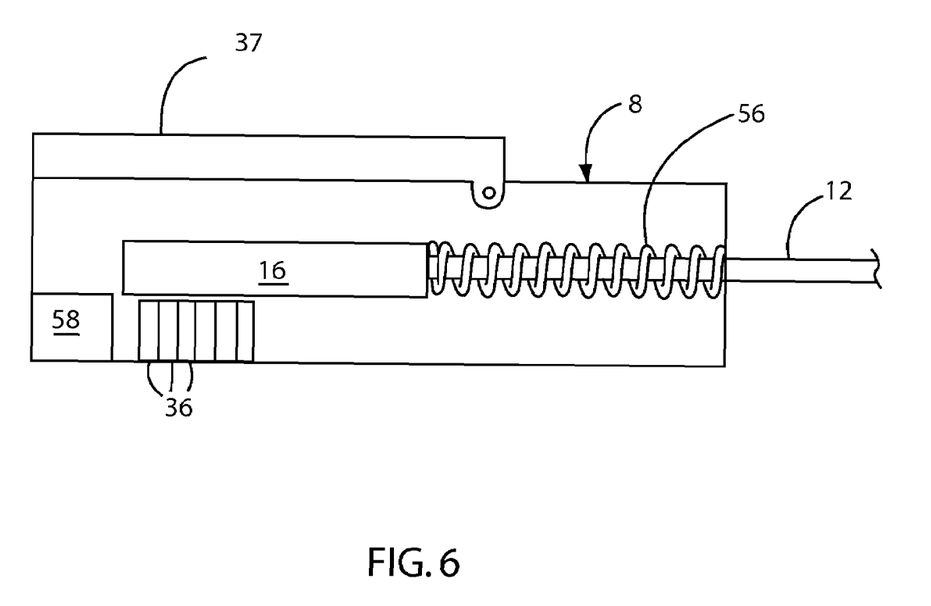
FIG. 6 is a schematic view of an exemplary stapler head.

Referring to FIG. 6, the slider 16 may be biased distally by a biasing element 56. As one example, the biasing element 56 may be a compression spring positioned between the proximal wall 24 of the slider 16 and the rear wall 54 of the inner surface of the housing 14. The compression spring may be substantially concentric with the force transmission member 12, or may be offset from the force transmission member 12. Alternately, the biasing element 56 may be any other structure, mechanism or combination thereof that biases the slider 16 distally. Alternately, the biasing element 56 may be omitted, such that the slider 16 is not biased distally.

The holders 36 may be indexed in the proximal direction. That is, an indexing mechanism 58 may be configured to move the holders 36 collectively in the proximal direction, one holder 36 at a time. This discrete motion of the holders 36 may be referred to as indexing. The indexing mechanism 58 moves the holders 36 sequentially into position over the ejection aperture 52, or facilitates this motion. The indexing mechanism 58 may be any mechanism capable of doing so. As one example, the indexing mechanism 58 may include a ratchet mechanism. A second force transmission member may be connected to the indexing mechanism 58, and may move proximally a distance substantially equal to the width of one holder 36 in order to index the holders 36. The second force transmission member may be controlled by a piston, spring, stepper motor or other suitable mechanism in the handle 4 or elsewhere.

The stapler head 8 may include a stabilizer 37. The stabilizer 37 is movable from a first position to a second position in order to stabilize the stapler head 8 in use, as described in greater detail below. The stabilizer 37 may be any mechanism that is configured to stabilizer the stapler head 8. As one example, the stabilizer 37 is a paddle or similar device movable relative to the stapler head 8. The stabilizer 37 may be hinged or otherwise connected to the stapler head 8, and may rotate about any axis or axes, or move in any suitable direction, between the first position and the second position. Optionally, a biasing element such as a spring may bias the stabilizer 37 to the first, stowed position. A force transmission member may connect the stabilizer 37 to the handle 4 directly or indirectly, such that the force transmission member controls the position of the stabilizer 37. Alternately, the stabilizer 37 may be a balloon or other inflatable structure that is connected to the stapler head 8, such as to the upper surface of the stapler head 8. The balloon 37 may be inflatable to stabilize the stapler head 8 in a desired location, and deflatable to allow movement of the stapler head 8 to a treatment site. The balloon 37 may be inflated by a fluid source in the handle 4, particularly where the handle 4 includes a fluid-driven actuator for actuating the stapler head 8; fluid such as pressurized gas may be transmitted to and from the balloon 37 via a lumen of the catheter 6. Alternately, the pressurized gas source or other fluid source may be located substantially within the stapler head 8. Alternately, the stabilizer 37 is not used. Alternately, the intravascular stapling tool 2 includes two opposed stapler heads 8 facing in substantially opposite directions, where neither stapler head 8 includes a stabilizer 37 The stapler heads 8 may be movable apart from and/or biased apart from one another, such that when both stapler heads 8 are in contact with tissue, each stapler head 8 stabilizes the other.

Operation

Figure 8:
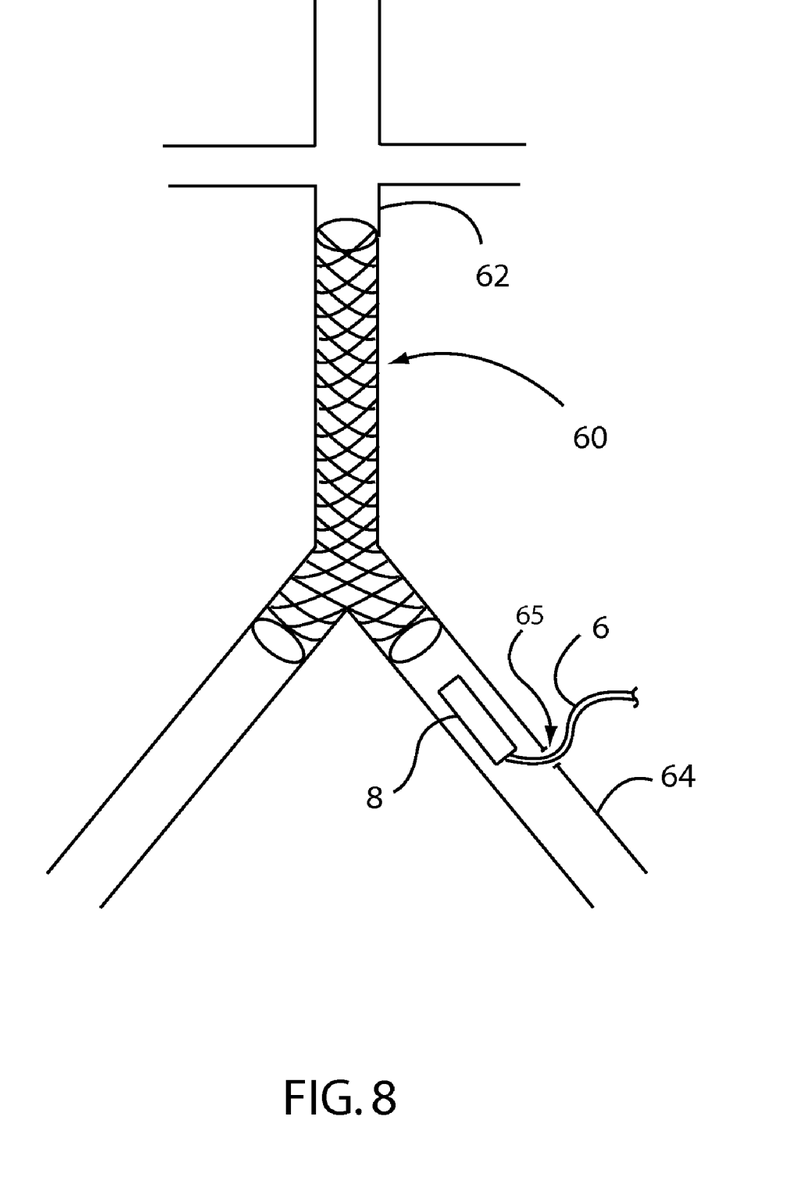
FIG. 8 is a schematic view of the placement of an AAA graft in the abdominal aorta utilizing the intravascular stapling tool.

Referring also to FIG. 8, to introduce the stapler head 8 into the vasculature of a patient, an incision 65 is made in the patient's femoral artery 64 in a standard manner. For the purpose of describing the operation of the intravascular stapling tool 2, the placement of a AAA graft 60 will be described. However, the intravascular stapling tool 2 may be utilized at a different location in the patient's vasculature. Further, the intravascular stapling tool 2 may be introduced into the vasculature via the radial artery or other blood vessel. Before inserting the stapler head 8 into the femoral artery 64, a AAA graft 60 may be advanced through the opening in the femoral artery into the abdominal aorta 62 and placed in its desired location. Alternately, the AAA graft 60 may be moved into its desired position in the aorta 62 along with the stapler head 8. Alternately, the AAA graft 60 may be moved into its desired position in the aorta 62 after the stapler head 8 has been moved into position.

The stapler head 8 is inserted through the opening in the femoral artery and advanced upward by pushing on the catheter 6. The catheter 6 may be configured to follow a guidewire that has been previously placed in the patient according to standard interventional cardiology practice, or may be configured to be advanced regardless of the presence of a guidewire. The stapler head 8 is thus advanced through the femoral artery into the abdominal aorta. Any suitable technique may be utilized to place the stapler head 8 in the desired position in the abdominal aorta. For example, at least part of the stapler head 8 may be radiopaque, such that an x-ray machine or the like in the operating room may be used to determine when the stapler head 8 has reached its final position.

When the stapler head 8 reaches its desired position, the stabilizer 37 is deployed, moving from a first (stowed) position to a second (stabilizing) position. Such deployment may be performed in any suitable manner. As one example, where the stabilizer 37 is a paddle or similar device movable relative to the stapler head 8, a force transmission member that connects the stabilizer 37 to the handle 4 directly or indirectly may be moved. As a result of motion of that force transmission member, the stabilizer 37 may rotate, expand or otherwise move into contact with an inner surface of the wall of the aorta 62, thus moving from the first position to the second position. This contact between the stabilizer 37 and the wall of the aorta 62 pushes the stapler head 8 into contact with a different part of the wall of the aorta 62 and/or with the AAA graft 60, such that the ejection aperture 52 is substantially adjacent to the wall of the aorta and/or the AAA graft 60. Alternately, where the stabilizer 37 is a balloon, the stabilizer is inflated from the first position to the second position. Alternately, where the stabilizer 37 is a different mechanism, the stabilizer 37 is actuated in any suitable manner. Alternately, where the stabilizer 37 is omitted, and two opposed stapler heads 8 are provided, the stapler heads 8 are moved apart from one another, such that each stapler head 8 contacts the wall of the aorta 62 and stabilizes the other. Optionally, the stapler head 8 and/or the handle 4 may include a safety mechanism that prevents deployment of a staple 38 until the stabilizer 37 is deployed.

Initially, the slider 16 is in an initial position, as shown in FIGS. 2-3. In the initial position of the slider 16, each post 30 of the driver 28 is positioned at the proximal end of the corresponding slot 22 in the wall 20 of the slider 16. The slot 22 is shaped to facilitate deployment of staples 38, as described in greater detail below. When the slider 16 is in the initial position, a holder 36 is positioned directly below the driver 28, and may be said to be in firing position. When the holder 36 is in firing position, it is above the ejection aperture 52 in the lower surface of the housing 14. Further, the driver 28 is initially in a ready position above the holder 36. The ready position may be the uppermost position that the driver 28 can occupy, or may be a different vertical position relative to the housing 14.

The user depresses the trigger 10, manipulates a different control, or otherwise actuates the intravascular stapling tool 2 after the stapler head 8 has reached the desired position. In this way, the intravascular stapling tool 2 may be actuated with a single input from a user. In response, the handle 4 moves the force transmission member 12 proximally. For example, where the force transmission member 12 is a cable, the handle 4 applies tension to that cable, moving it proximally. This proximal motion of the force transmission member 12 moves the slider 16 proximally. Each post 30 of the driver 28 is constrained against horizontal motion and restricted to vertical motion by the corresponding groove 32. Thus, as the slider 16 moves proximally, each slot 22 in the wall 20 of the slider 16 acts to move the corresponding post 30 vertically. That is, the shape of the slot 22 controls the vertical motion of the corresponding post 30, and thus the vertical motion of the driver 28.

The exemplary slot 22 is substantially horizontal for a short distance extending distally from its proximal end, such that proximal motion of the slider 16 initially does not move the corresponding post 30 and thus the driver 28 vertically. This horizontal portion of the slot 22 provides extra safety, such that negligible motion of the force transmission member 20 does not cause vertical motion of the driver 28.

Looking distally along the slider 16, a first portion 23 of the slot 22 extends downward at a first angle from horizontal. As the first portion 23 of the slot 22 is pulled proximally, the first portion 23 urges the corresponding post 30 downward in the corresponding groove 32, thus urging the driver 28 downward. The driver 28 contacts the base 40 of the staple 38 that is located in the holder 36 in firing position. Advantageously, the shape of the driver 28 and the shape of the base 40 facilitate contact and force transmission therebetween. For example, where the base 40 of the staple is substantially rectangular, the driver 28 may include a substantially rectangular surface that is similar in size to the base 40 of the staple 40 to spread the contact force therebetween over a larger area.

As the driver 28 continues to move downward, it pushes the staple 38 within the holder 36 toward the ejection aperture 52. The end of each tine 42 of the staple 38 contacts the corresponding ramp element 48 of the holder 36. This contact causes each tine 42 to begin to bend as the staple 38 moves toward the ejection aperture 52. Referring also to FIG. 8, as the tines 42 move out of the ejection aperture 52, they penetrate the AAA graft 60, and then the tissue of the aorta 62. The angle of each slot 22 immediately distal to the horizontal portion of the slot 22 assists in the penetration of the AAA graft 60 and the tissue of the aorta 62 by causing substantial vertical motion in a short period of time. That is, because the slider 16 may be moved horizontally by the force transmission member 12 at substantially a constant rate, the angle of the slot 22 relative to the horizontal at any given point controls the rate of vertical motion of the driver 28. The greater the angle from horizontal, the more rapid the vertical motion.

Moving further distally along the slider 16, a second portion 25 of the slot 22 extends downward at a second angle from horizontal. As the second portion 25 of the slot 22 is pulled proximally, the second portion 25 urges the corresponding post 30 downward in the corresponding groove 32, thus continuing to urge the driver 28 downward. The second angle is less than the first angle, relative to the horizontal. The second portion of each slot 22 immediately distal to the first portion of that slot 22 spreads vertical motion of the driver 28 over a longer time than the first portion of that slot 22, because the force required for forming the staple 38 is less than the potential force required to urge the tines 42 of the staple 38 through the AAA graft and the tissue of the aorta. Alternately, the second angle is the same as the first angle, or is greater than the first angle. As the driver 28 continues to move downward, it continues to push toward the ejection aperture 52 the staple 38 that is within the holder 36 underneath the driver 28. The end of each tine 42 of the staple 38 continues to contact the corresponding ramp element 48 of the holder 36 as the driver 28 continues to move downward. This contact causes each tine 42 to continue to bend as the staple 38 moves toward the ejection aperture 52. The curvature of each ramp element 48 in proximity to the corresponding foot 50 determines the path along which each tine 42 travels as it moves through the AAA graft and the tissue of the aorta. Advantageously, the curvature of each ramp element 48 in proximity to the corresponding foot 50 directs the corresponding tine 42 along a path that does not snag tissue outside of the aorta.

Each foot 50 controls the entry point of the corresponding tine 42 into tissue, and controls the path of each tine 42 into tissue during staple forming. In this way, the feet 50 prevent bunching of the tissue as the staple 38 is formed. Bunching refers to the undesirable effect on tissue of the tines of a traditional surgical staple when the staple is closed and the tines are brought closer together. With a traditional staple and stapler, this motion pushes tissue between the tines together, thereby bunching the tissue, and also may create holes in tissue as the tines stretch tissue that is not trapped between the tines. Each foot 50 provides a known location at which the tine 42 is controlled to exit the corresponding holder 36. That is, each foot 50 guides the corresponding tine 42 through tissue substantially along a path determined by that foot 50. As a result, during staple forming, the location of each tine 42 relative to its penetration of tissue is substantially constant. That is, the location on the tissue that is penetrated by the tine 42 of a staple 38, which may be referred to as the tine entry point, is substantially constant throughout the process of deploying the staple 38. The tine entry point is not substantially enlarged or moved during deployment. Because the location at which each tine 42 penetrates the tissue of the aorta 62 is substantially the same throughout the staple forming process, bunching is substantially prevented.

Figure 7:
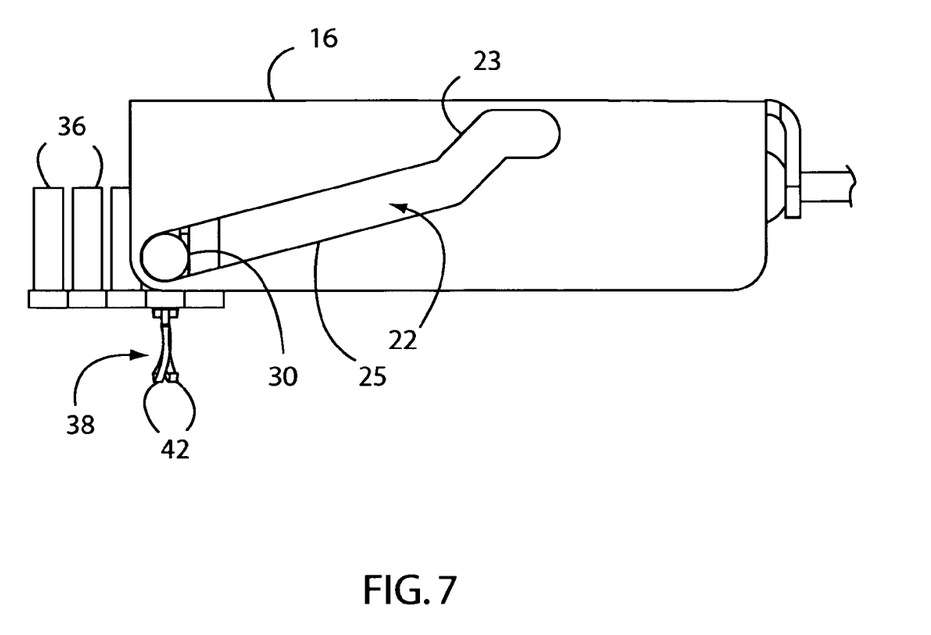
FIG. 7 is a side view of a slider of the stapler head in a second position.

Referring also to FIG. 7, as the staple 38 is formed, the tines 42 swipe past each other. In this way, the tines 42 do not substantially interfere with one another, substantially preventing uncontrolled deflections that may result from such interference. The tines 42 may be configured to swipe past one another in any suitable manner. As one example, the ramp elements 48 are angled differently from one another and/or the feet 50 are slightly offset from one another, such that the tines 42 are controlled to swipe past one another. As another example, the staple 38 is fabricated to result in the tines 42 swiping past one another. The staple 38 may be fabricated such that the tines 42 are offset from one another before deployment; cutouts or weakened areas in one or both tines 42 of the staple 38 may provide for preferential bending of the tines 42 in directions that result in the tines 42 swiping past each other, or the staple 38 may have other properties that result in its tines 42 swiping past each other.

Referring also to FIG. 7, the slider 16 has reached the end of its travel, with at least one post 30 of the driver 28 contacting the distal end of the corresponding slot 22. At this point, the staple 38 is fully formed. The process of urging the tines of the staple 38 into tissue and forming the staple 38 may be referred to as deployment. The feet 50 and ramp elements 48 may control the tines 42 such that their ends are substantially tangent to the outer surface of the wall of the aorta and such that the tines 42 lie against or close to the outer surface of the wall of the aorta. Thus, after the staple 38 has been fully formed, it secures the AAA graft to the wall of the aorta, and is itself secured to tissue. Nothing remains to hold the staple 38 within the holder 36, and the base 40 of the staple 38 moves out of the bottom of the holder 36 and through the ejection aperture 52. The staple 38 is thus released from the stapler head 8.

Next, tension on the force transmission member 12 is released. As a result, the force transmission member 12 exerts no force or a reduced force in the distal direction on the slider 16. The biasing element 56 exerts a distal force on the slider 16, moving it back toward its initial position. Alternately, the force transmission member 12 is substantially rigid and is moved distally, and the biasing element 56 is omitted. As the slider 16 moves distally, each post 30 of the driver 28 moves along the corresponding slot 22 in a manner opposite to its motion during deployment of the staple 38, such that the driver 28 moves upward to its initial position as a result. Next, the indexing mechanism 58 moves the holders 36 collectively in the proximal direction, by a distance substantially equal to the width of one holder 36. In this way, another holder 36 containing a staple 38 may be moved into the firing position between the driver 28 and the ejection aperture 52. As one example of operation, a second force transmission member is connected to the indexing mechanism, and moves proximally a distance substantially equal to the width of one holder 36 in order to index the holders 36. The second force transmission member may be controlled by a piston, spring, stepper motor or other suitable mechanism in the handle 4 or elsewhere. As another example, a biasing element acts in concert with a ratchet mechanism in the stapler head 8 to index the holders 36. The holders 36 may be indexed in any suitable manner. The stapler head 8 is thus ready to fire again, utilizing the process described above.

Next, the stabilizer 37 is moved from the second position to the first position, freeing the stapler head 8 to move relative to the aorta 62. Such movement may be performed in any suitable manner, such as by performing actions that are substantially the opposite of those actions performed to move the stabilizer 37 from the first position to the second position. As one example, the stabilizer 37 may be biased to the first position, and tension may be released on the force transmission member holding the stabilizer 37 in the second position such that the biasing force on the stabilizer 37 returns it to the first position. As another example, the stabilizer 37 may be deflated. A number of staples 38 may need to be placed to secure the AAA graft 60 to the aorta 62. The handle 4 may be rotated and/or moved longitudinally along the aorta 62 to position the stapler head 8 in a different position for deploying another staple 38. Such motion of the handle 4 causes motion of the catheter 6, which in turn causes motion of the stapler head 8. Alternately, a rotary mechanism (not shown) in the handle 4 is used to rotate the stapler head 8 without having to rotate the entire handle 4. The stapler head 8 may be moved into each femoral artery 64 in proximity to the lower portion of the AAA graft 60 to staple that portion of the AAA graft 60 to the tissue of the femoral artery 64. The femoral artery 64 other than that in which the incision 65 is made may be accessed by steering the stapler head 8 via the catheter 6 using any standard catheter guidance method. Alternately, an incision is made in the other femoral artery 64, and the stapler head 8 is inserted through that incision to staple the AAA graft 60 to that femoral artery 64 and complete the procedure.

In the course of operation of the intravascular stapling tool, the force transmission member 12 and other force transmission members may be manipulated as described above by any suitable mechanism or mechanisms. Thus, the particular configuration of the handle 4 is not critical, because it may be configured in any manner that controls the force transmission members as described above. As one example, the handle 4 may include a fluid-driven actuator that utilizes a working fluid such as compressed gas to drive one or more pistons in response to the actuation of the trigger 10; the force transmission member 12 may be coupled to one of those pistons, as may one or more other force transmission members. In this way, motion of the pistons causes motion of the corresponding force transmission member 12. Such a fluid-driven actuator is described in U.S. patent application Ser. No. 11/054, 265, filed Feb. 9, 2005, entitled "Anastomosis Tool Actuated with Stored Energy," which is hereby incorporated by reference in its entirety. Alternately, the handle 4 may include any other mechanism or mechanisms that manipulate the force transmission members 12 as described above after actuation of the trigger 10.

While the invention has been described in detail, it will be apparent to one skilled in the art that various changes and modifications can be made and equivalents employed, without departing from the present invention. It is to be understood that the invention is not limited to the details of construction, the arrangements of components and/or the details of operation set forth in the above description or illustrated in the drawings. Headings and subheadings are for the convenience of the reader only. They should not and cannot be construed to have any substantive significance, meaning or interpretation, and should not and cannot be deemed to be limiting in any way, or indicate that all of the information relating to any particular topic is to be found under or limited to any particular heading or subheading. The contents of each section of this document are merely exemplary and do not limit the scope of the invention or the interpretation of the claims. Therefore, the invention is not to be restricted or limited except in accordance with the following claims and their legal equivalents.

What is claimed is:

1. A method for stapling tissue in an animal body having a vasculature composed of tissue, comprising:

providing an intravascular stapling tool including a stapler head connected to a catheter, wherein said stapler head includes at least a first holder and a second holder, each said holder including two columns between which a staple is held, said staple including a plurality of tines, and wherein each column includes on an inner surface thereof a ramp element curved inward toward the bottom of said column, each said ramp element terminating in a foot, wherein said holders are oriented generally parallel to one another;

creating an incision in a peripheral vessel;

inserting the stapler head through said incision;

utilizing said catheter to advance said stapler head along the vasculature; and urging one said staple to exit the corresponding said first holder, said first holder located in a deployment position, such that said tines of said staple deform inward as a result of contact between the distal ends of said tines against corresponding said ramp elements and feet;

indexing said holders substantially linearly such that said first holder moves out of said deployment position and said second holder moved into said deployment position; and then urging one said staple out of said second holder, such that said tines of said staple deform inward as a result of contact between the distal ends of said tines against corresponding said ramp elements and feet.

2. The method of claim 1, incorporating by reference all of the limitations of that claim, wherein the peripheral vessel is a femoral artery.

3. The method of claim 1, incorporating by reference all of the limitations of that claim, wherein said intravascular stapling tool includes a handle connected to said catheter; wherein said urging is performed in response to a single user input to said handle.

4. The method of claim 1, incorporating by reference all of the limitations of that claim, further comprising providing an abdominal aortic aneurysm graft; wherein said urging attaches said abdominal aortic aneurysm graft to tissue.

5. The method of claim 1, incorporating by reference all of the limitations of that claim, wherein said stapler head includes a stabilizer; further comprising moving said stabilizer into contact with tissue, and wherein said moving pushes said stapler head against tissue.

6. The method of claim 5, incorporating by reference all of the limitations of that claim, wherein said moving comprises rotating said stabilizer relative to a remainder of said stapler head.

7. The method of claim 5, incorporating by reference all of the limitations of that claim, wherein said moving comprises expanding said stabilizer.

8. The method of claim 1, incorporating by reference all of the limitations of that claim, wherein said urging maintains the entry point of each tine into tissue substantially constant for the duration of said urging.

* * * * *